United States Patent
Tinti

(10) Patent No.: US 7,858,820 B2
(45) Date of Patent: Dec. 28, 2010

(54) SOLID COMPOSITIONS SUITABLE FOR ORAL ADMINISTRATION CONTAINING NON-HYGROSCOPIC SALTS OF L-CARNITINE AND THE ALKANOYL L-CARNITINES WITH TAURINE CHLORIDE AND GLYCINE CHLORIDE

(75) Inventor: Maria Ornella Tinti, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 909 days.

(21) Appl. No.: 10/415,472

(22) PCT Filed: Sep. 28, 2001

(86) PCT No.: PCT/IT01/00503

§ 371 (c)(1),
(2), (4) Date: Apr. 30, 2003

(87) PCT Pub. No.: WO02/36543

PCT Pub. Date: May 10, 2002

(65) Prior Publication Data

US 2004/0024061 A1 Feb. 5, 2004

(30) Foreign Application Priority Data

Sep. 28, 2001 (IT) .................. RM2000A0567

(51) Int. Cl.
*C07C 229/00* (2006.01)
*C07C 309/00* (2006.01)
(52) U.S. Cl. ....................................... 560/125; 562/104
(58) Field of Classification Search ................. 514/547, 514/556; 560/125; 562/104
See application file for complete search history.

(56) References Cited

U.S. PATENT DOCUMENTS 6,124,360 A * 9/2000 Scafetta et al. .............. 514/556

FOREIGN PATENT DOCUMENTS

| EP | 0 150 688 A | | 8/1985 |
|---|---|---|---|
| WO | 98/43945 A | | 10/1998 |
| WO | WO 98/43945 | * | 10/1998 |
| WO | 00/73258 A | | 12/2000 |
| WO | WO 00/73258 | * | 12/2000 |

* cited by examiner

*Primary Examiner*—Alton N Pryor
(74) *Attorney, Agent, or Firm*—Lucas & Mercanti, LLP

(57) ABSTRACT

Described herein are both non-hygroscopic salts of L-carnitine and alkanoyl L-carnitine with taurine chloride (2-aminoethane-sulphonic chloride) and non-hygroscopic salts of L-carnitine and alkanoyl L-carnitine with glycine chloride which lend themselves favorably to the preparation of solid compositions suitable for oral administration. Also described are solid compositions containing said salts.

2 Claims, No Drawings

SOLID COMPOSITIONS SUITABLE FOR ORAL ADMINISTRATION CONTAINING NON-HYGROSCOPIC SALTS OF L-CARNITINE AND THE ALKANOYL L-CARNITINES WITH TAURINE CHLORIDE AND GLYCINE CHLORIDE

This application is the US national phase of international application PCT/IT01/00503 filed 28 Sep. 2001, which designated the US.

The invention described herein relates to physiologically acceptable salts of L-carnitine and alkanoyl L-carnitine, characterised in that they are non-hygroscopic and stable. Said salts lend themselves favourably to the preparation of solid compositions suitable for oral administration. The invention also relates to pharmaceutical and alimentary or nutritional compositions containing them.

It is well known that carnitine and its alkanoyl derivatives lend themselves to various therapeutic uses. For example, L-carnitine is used in the cardiovascular field for the treatment of acute and chronic myocardial ischaemia, angina pectoris, heart failure and cardiac arrhythmias.

In the nephrological field, L-carnitine is administered to uraemic patients on regular haemodialysis treatment to combat muscular asthenia and the onset of muscle cramps.

Other therapeutic uses relate to the restoration of a normal HDL/LDL+VLDL ratio and total parenteral nutrition.

It is also well known that the salts of L-carnitine and its alkanoyl derivatives known to date present the same therapeutic or nutritional activities as the so-called "inner salts" and can therefore be used in their place, provided such salts are "physiologically acceptable", that is to say they do not present toxic or unwanted side effects.

In practice, then, the choice between an inner salt and an actual salt of L-carnitine or alkanoyl L-carnitine has depended to date exclusively on which compound was more easily or economically available and on considerations of pharmaceutical technology rather than on considerations of therapeutic or nutritional activity.

The purpose of the invention described herein is to provide stable, non-hygroscopic salts of L-carnitine and the lower alkanoyl L-carnitines that present in addition an increased therapeutic and/or nutritional value compared to the corresponding inner salts.

It should therefore be clearly understood that the usefulness of the salts according to the invention described herein consists not only in their non-hygroscopicity and their greater stability compared to the corresponding inner salts, but also in the fact that their anionic part contributes to the therapeutic and/or nutritional value of the salt as a whole, such value therefore not being exclusively determined by the "carnitine" part of the salt.

The non-hygroscopicity of these salts makes them easier to process, particularly in view of the preparation of solid oral administration forms.

As experts in pharmaceutical technology are well aware, the processing of hygroscopic products entails the use of controlled humidity chambers for both storage and processing.

In addition, the finished product must be packaged in hermetically sealed blister packs to avoid the disagreeable consequences of humidity.

All this implies greater storage costs for the raw materials and for their processing and packaging.

Among the populations of the industrialised countries there is an increasing use of food supplements or "nutraceuticals" by sportsmen (amateurs or professionals) and also by people in a good state of health.

Sportsmen use L-carnitine or food supplements containing carnitine because it favours the oxidation of fatty acids and makes available a greater amount of energy to skeletal muscle, thus permitting enhanced performance and giving rise to less accumulation of lactic acid in the athletes' muscles.

People in a good state of health use these food supplements as health foods, i.e. for the purposes of favouring a reduction in serum levels of fats and restoration of a normal ratio between the various cholesterol fractions with a view to preventing diseases related to lipid metabolism disorders.

It has been estimated that the amount of L-carnitine and its derivatives sold for non-ethical purposes is twice that sold for ethical purposes.

The US market for health foods or nutraceuticals amounts to approximately 250 billion dollars, whereas the estimated figure for the European market is around 500 billion dollars (Food Labeling News, 1994, "Nutraceuticals" Market said to be a vast one, March, Vol. 2, N° 25; King Communications Group Inc., 1993, "Nutraceuticals" Foods, Drink in Global Market, Food and Drink Daily, April, Vol. 3, N° 503).

A number of non-hygroscopic salts of L-carnitine or the alkanoyl L-carnitines are already known.

For example, European patent 0 434 080 (Lonza) filed on Dec. 21, 1990 describes the use of a non-hygroscopic salt of L-carnitine with L(+)-tartaric acid (salt already described by Müller and Strack in Hoppe-Seyler's Z. Physiol. Chem., 353, 618-622, April 1972) for the preparation of solid oral administration forms.

This salt, however, presents a number of drawbacks, such as, for instance, the release of trimethylamine after prolonged storage, which produces a disagreeable odour due to the characteristic fishy smell of this amine.

In addition, L-(+)-tartaric acid is not capable of furnishing non-hygroscopic salts with alkanoyl L-carnitines such as, for example, acetyl L-carnitine.

It should also be noted that the tartrate anion is not capable, alone, of increasing the therapeutic and/or nutritional value of carnitine.

U.S. Pat. No. 4,602,039 (Sigma Tau) describes the fumarates of L-carnitine, acetyl L-carnitine and propionyl L-carnitine.

While L-carnitine fumarate is highly non-hygroscopic, resisting even better than L-carnitine tartrate in a milieu with a high relative humidity content, this property seems to diminish on increasing the weight of the alkanoyl radical.

WO98/43945 describes solid compositions suitable for oral administration containing non-hygroscopic salts of L-carnitine and the alkanoyl L-carnitines with 2 aminoethanesulphonic acid (taurine).

WO98/45250 describes solid compositions suitable for oral administration containing L-carnitine and alkanoyl L-carnitine magnesium tartrate.

WO98/44918 describes solid compositions suitable for oral administration containing alkanoyl L-carnitine magnesium citrate.

WO98/47857 describes solid compositions suitable for oral administration containing L-carnitine choline tartrate or alkanoyl L-carnitine choline tartrate.

WO98/49134 describes solid compositions suitable for oral administration containing L-carnitine and alkanoyl L-carnitine magnesium fumarate.

The above-mentioned purpose of the invention described herein is therefore to form new pharmacologically acceptable non-hygroscopic, stable salts of both L-carnitine and the lower alkanoyl L-carnitines in which the anionic part contributes to the therapeutic and/or nutritional value of the salt.

The object of the invention described herein is therefore a salt of L-carnitine with taurine chloride (chloride salt of 2-amino-ethane-sulphonic acid) of general formula (I)

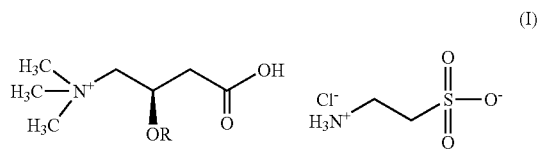

(I)

wherein R is hydrogen or a straight or branched lower alkanoyl, with 2-5 carbon atoms.

The salts in which R is selected from the group consisting of acetyl, propionyl, butyryl, valeryl and isovaleryl are to be preferred.

As mentioned above, international patent application WO98/43945 filed in the name of the applicant describes solid compositions suitable for oral administration containing non-hygroscopic carnitine salts with 2-aminoethanesulphonic acid, whereas the salts of the invention described herein are carnitine salts with the chloride salt of 2-aminoethanesulphonic acid.

Reading WO98/43945 the expert in the sector would have expected to obtain carnitine salts with the chloride salt of 2-amino-ethane-sulphonic acid endowed with a hygroscopicity similar to that of the salts described in WO98/43945.

The unexpected lower hygroscopicity of the salts according to the invention described herein, compared with the salts described in WO98/43945, makes them particularly useful for the preparation of solid oral compositions suitable for the above-mentioned purposes.

A further object of the invention described herein is a salt of L-carnitine with glycine chloride of general formula (II)

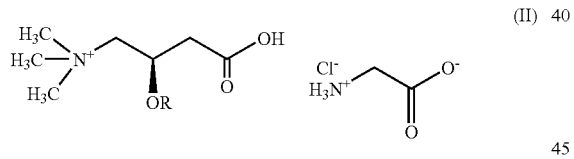

(II)

where R is hydrogen or a straight or branched lower alkanoyl, with 2-5 carbon atoms. The salts in which R is selected from the group consisting of acetyl, propionyl, butyryl, valeryl and isovaleryl are to be preferred.

Taurine is one of the most abundant amino acids in the body and is to be found in the central nervous system and in skeletal muscle and is moreover concentrated in the brain and heart. It has been known for some time now to be an essential nutrient during the growth and development of mammals; in fact, it is present in mother's milk and is especially important for the development of the cerebellum and retina. Taurine also has a very important metabolic function: in bile, the bile acids are bound to taurine to form the glycocholic and taurocholic acids, respectively.

The salts of bile acids possess the important property of lowering the surface tension of solutions. For this reason they are excellent emulsifying agents and perform an important function in the absorption and digestion of lipids in the bowel.

These important metabolic and nutritional characteristics mean that taurine when bound to L-carnitine performs a complementary function to that performed by L-carnitine. In fact, by favouring the emulsification and digestion of fatty acids, taurine is complementary to the subsequent metabolic activity exerted by L-carnitine, i.e. the oxidation of fatty acids for energy production.

Glycine is an important amino acid widely used as a food supplement both in human nutrition and in the feeding of livestock and pets. Thus, the non-hygroscopic salt of carnitine with glycine also presents an enhanced therapeutic and/or nutritional value compared to the corresponding inner salt, in that, as already mentioned, the anionic part (glycine) contributes to the therapeutic and/or nutritional value which is therefore no longer determined exclusively by the "carnitine" part of the salt.

The non-hygroscopic salts according to the invention described herein are useful agents in human or animal nutrition both in physiological conditions, i.e. in subjects in a good state of health, and in the malabsorption syndromes observed in children and adults.

The salts of L-carnitine and the lower alkanoyl L-carnitines according to the invention described herein are non-hygroscopic, are easy to process and are highly stable on storage.

Given here below are same examples for the preparation of the non-hygroscopic salts according to the invention.

EXAMPLE 1

Procedure for the Preparation of Acetyl L-Carnitine Salt with Taurine Chloride (ST 1805)

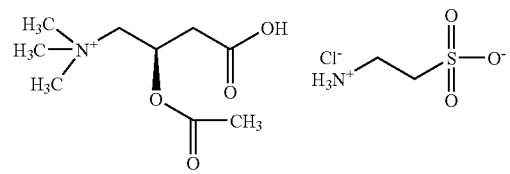

2.5 g of taurine [0.02 mol] and 4.78 g of acetyl L-carnitine chloride [0.02 mol] were dissolved in the minimal amount of water and vacuum concentrated at 40° C. The residue thus obtained was extracted with acetone and held overnight under stirring and then filtered and dried.

7.1 g of a non-hygroscopic white crystalline solid were obtained.

Yield: 76%.

DSC=186° C. by decomposition.

NMR in solid phase $^{13}C$ ppm 67.0 (CH—O); 63.6 (N$^+$—$\underline{CH_2}$—CH), 54.1 ((CH$_3$)$_3$N$^+$); 46.6 (N$^+\underline{CH_2}$—CH$_2$); 36.4 ($\underline{CH_2}$CO, CH$_2$S); 21.9 (CH$_3$)

NMR: D$_2$O Hδ 5.6-5.5 (1H, m, —CH—); 3.8-3.6 (2H, m, N—$\underline{CH_2}$); 3.4-3.3 (2H, t, H$_2$N—$\underline{CH_2}$); 3.2-3.1 (2H, t, CH₂—SO₃—); 3 (9H, s, (CH₃)₃—N); 2.8-2.7 (2H, d, CH₂—COOH); 2 (3H, s, COCH₃)

EXAMPLE 2

Procedure for the Preparation of Propionyl L-Carnitine Salt with Taurine Chloride (ST 1806)

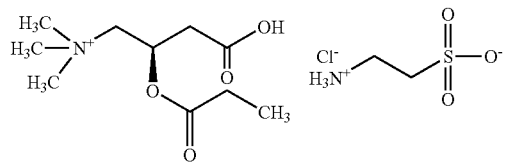

2.5 g of taurine [0.02 mol] and 5.1 g of propionyl L-carnitine chloride [0.02 mol] were dissolved in the minimal amount of water and vacuum concentrated at 40° C. The residue thus obtained was extracted with acetone, held overnight under stirring, filtered and dried.

7.2 g of a non-hygroscopic white crystalline solid were obtained.

Yield: 98%.

DSC 175° C. by decomposition.

NMR in solid phase $^{13}C$ ppm 69.5 (CH—O); 66.4 (N⁺—CH₂—CH), 53.9 ((CH₃)₃); 46.5 (N⁺CH₂—CH₂); 36.1 (CH₂CO, CH₂S); 29.6 (OCO CH₂); 10.4 (CH₃)

NMR: D₂O Hδ 5.6-5.5 (1H, m, —CH—); 3.8-3.6 (2H, m, N—CH₂); 3.4-3.3 (2H, t, H₂N—CH₂); 3.2-3.1 (2H, t, CH₂—SO₃—); 3.1 (9H, S, (CH₃)₃—N); 2.7-2.6 (2H, m, CH₂—COOH); 2.4-2.3 (2H, q, CH₂CH₃); 1-0.9 (3H, t, CH₂—CH₃)

EXAMPLE 3

Procedure for the Preparation of Acetyl L-Carnitine Salt with Glycine Chloride ST 1803

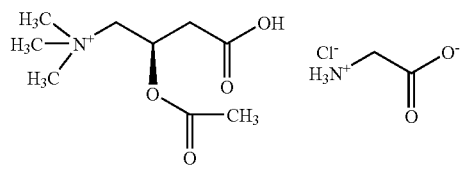

2.2 g of glycine hydrochloride (hygroscopic product) [0.02 mol] and 4.06 g of acetyl L-carnitine inner salt (hygroscopic product) [0.02 mol] were dissolved in 50 ml of water and vacuum concentrated.

The residue was extracted with acetone and held overnight under stirring and filtered.

The filtrate was vacuum dried at 30° C.

6.1 g of glycine hydrochloride acetyl L-carnitine salt were obtained in the form of a non-hygroscopic white crystalline solid.

Yield: 95%.

DSC=177° C. by decomposition

NMR in solid phase $^{13}C$ ppm 67.0 (CH—O); 63.8 (N⁺—CH₂), 54.5 ((CH₃)₃N⁺); 42.6 (N—CH₂—CO); 36.3 (CH₂CO); 27.1 (CH₃)

NMR: D₂O Hδ 5.6-5.5 (1H, m, —CH—); 3.7-3.5 (2H, m, N—CH₂); 3.5 (2H, s, H₂N—CH₂); 3.1 (9H, s, (CH₃)₃—N); 2.6-2.4 (2H, m, CH₂—COOH); 2 (3H, s, CO—CH₃)

EXAMPLE 4

Procedure for the Preparation of Propionyl L-Carnitine Salt with Glycine Chloride ST 1804

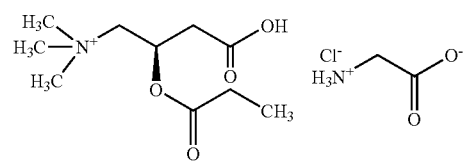

2.2 g [0.02 mol] of glycine hydrochloride (hygroscopic product) and 4.35 g of propionyl L-carnitine inner salt (hygroscopic product) [0.02 mol] were dissolved in the minimal amount of water and vacuum concentrated. The residue thus obtained was extracted with acetone and held overnight under stirring and then filtered and dried.

6.2 g of a non-hygroscopic white crystalline solid were obtained.

Yield: 94%.

DSC=163° C.

NMR in solid phase $^{13}C$ ppm 69.5 (CH—O); 66.4 (N⁺—CH₂), 53.8 ((CH₃)₃N⁺); 43.1 (N—CH₂—CO); 35.1 (CH₂CO); 29.6 (OCOCH₂); 13.3 (CH₃)

NMR: D₂O Hδ=5.6-5.5 (1H, m, —CH—); 3.7-3.5 (2H, m, N—CH₂); 3.5 (2H, s, H₂N—CH₂); 3.1 (9H, s, (CH₃)₃—N—); 2.7-2.6 (2H, m, CH₂—COOH); 2.4-2.3 (2H, q, CH₂—CH₃); 1-0.9 (3H, t, CH₂CH₃)

The compounds in the examples mentioned are non-hygroscopic and highly stable.

The invention described herein also covers compositions containing as their active ingredient at least one of the above-mentioned pharmacologically acceptable non-hygroscopic salts well known to experts in pharmaceutical and food technology and possibly one or more additional active ingredients.

Particularly preferred are compositions in solid form suitable for the preparation of oral administration forms as tablets, chewable tablets or capsules containing a salt of L-carnitine or alkanoyl L-carnitine of formula (I) or (II) corresponding to 50-2000, and preferably 100-1000 mg of L-carnitine or alkanoyl L-carnitine expressed as an inner salt.

For example, a composition suitable for the production of tablets is the following:

| Non-hygroscopic salt of L-carnitine | |
|---|---|
| according to the invention | 500 mg |
| Starch | 20 mg |
| Talc | 10 mg |
| Ca-stearate | 1 mg |
| | 531 mg |

A composition suitable for the production of capsules is the following:

| Non-hygroscopic salt of L-carnitine | |
|---|---|
| according to the invention | 500 mg |
| Lactose | 50 mg |
| Starch | 20 mg |
| Talc | 5 mg |
| Ca-stearate | 2 mg |
| | 577 mg |

The invention claimed is:

1. A solid, stable, non-hygroscopic salt of L-carnitine or alkanoyl L-carnitine with taurine chloride of formula (I):

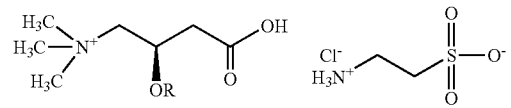

(I)

where R is hydrogen or a straight or branched lower alkanoyl with 2-5 carbon atoms.

2. The salt according to claim 1, where R is selected from the group consisting of acetyl, propionyl, butyryl, valeryl or isovaleryl.

* * * * *